US009566256B2

(12) United States Patent
Carter et al.

(10) Patent No.: US 9,566,256 B2
(45) Date of Patent: Feb. 14, 2017

(54) TRANSDERMAL DRUG DELIVERY USING AN OSMOLYTE AND VASOACTIVE AGENT

(75) Inventors: Stephen G. Carter, Andover, MA (US); Zhen Zhu, Andover, MA (US); Kanu Patel, Londonderry, NH (US); John J. Masiz, Topsfield, MA (US)

(73) Assignee: Biochemics, Inc., Danvers, MA (US)

( * ) Notice: Subject to any disclaimer, the term of this patent is extended or adjusted under 35 U.S.C. 154(b) by 423 days.

(21) Appl. No.: 12/564,841

(22) Filed: Sep. 22, 2009

(65) Prior Publication Data

US 2010/0076035 A1 Mar. 25, 2010

Related U.S. Application Data

(60) Provisional application No. 61/099,129, filed on Sep. 22, 2008.

(51) Int. Cl.
| | |
|---|---|
| A61K 47/26 | (2006.01) |
| A61K 31/192 | (2006.01) |
| A61K 31/415 | (2006.01) |
| A61K 9/00 | (2006.01) |
| A61K 9/06 | (2006.01) |
| A61K 31/05 | (2006.01) |
| A61K 31/19 | (2006.01) |
| A61K 31/426 | (2006.01) |
| A61K 45/06 | (2006.01) |
| A61K 47/02 | (2006.01) |
| A61K 31/455 | (2006.01) |
| A61K 31/427 | (2006.01) |
| A61K 47/22 | (2006.01) |
| A61F 13/00 | (2006.01) |

(52) U.S. Cl.
CPC ........... *A61K 31/192* (2013.01); *A61K 9/0014* (2013.01); *A61K 9/06* (2013.01); *A61K 31/05* (2013.01); *A61K 31/19* (2013.01); *A61K 31/415* (2013.01); *A61K 31/426* (2013.01); *A61K 31/427* (2013.01); *A61K 31/455* (2013.01); *A61K 45/06* (2013.01); *A61K 47/02* (2013.01); *A61K 47/22* (2013.01); *A61K 47/26* (2013.01); *A61F 2013/00906* (2013.01)

(58) Field of Classification Search
None
See application file for complete search history.

(56) References Cited

U.S. PATENT DOCUMENTS

| 4,440,777 A | 4/1984 | Zupan ........................... 424/274 |
|---|---|---|
| 4,758,599 A | 7/1988 | Minetti ......................... 514/844 |
| 4,830,856 A | 5/1989 | Peppers ........................ 424/449 |
| 4,933,184 A | 6/1990 | Tsuk .............................. 424/449 |
| 5,229,130 A | 7/1993 | Sharma et al. ............... 424/449 |
| 5,451,407 A | 9/1995 | Cormier et al. .............. 424/448 |
| 5,451,704 A | 9/1995 | Ho et al. ....................... 585/512 |
| 5,460,821 A | 10/1995 | Masiz ........................... 424/449 |
| 5,496,827 A | 3/1996 | Patrick ......................... 514/310 |
| 5,527,530 A | 6/1996 | Simmons et al. ............ 424/401 |
| 5,645,854 A | 7/1997 | Masiz ........................... 424/449 |
| 5,853,751 A | 12/1998 | Masiz ........................... 424/449 |
| 5,895,649 A | 4/1999 | De Lacharriere et al. ... 424/130 |
| 5,895,658 A | 4/1999 | Fossel .......................... 424/401 |
| 5,922,332 A | 7/1999 | Fossel .......................... 424/401 |
| 5,932,215 A | 8/1999 | De Lacharriere et al. 424/158.1 |
| 5,980,882 A | 11/1999 | Eichman .................... 424/78.12 |
| 6,015,835 A * | 1/2000 | Miyamoto et al. ........... 514/562 |
| 6,207,713 B1 | 3/2001 | Fossel .......................... 514/565 |
| 6,228,873 B1 * | 5/2001 | Brandt et al. ................. 514/347 |
| 6,248,763 B1 * | 6/2001 | Scivoletto .................... 514/356 |
| 6,306,130 B1 | 10/2001 | Anderson et al. ............ 606/27 |
| 6,321,909 B1 | 11/2001 | Wicomb et al. .............. 206/438 |
| 6,458,841 B2 | 10/2002 | Fossel .......................... 514/565 |
| 6,477,410 B1 | 11/2002 | Henley et al. ................. 604/20 |
| 6,486,206 B1 | 11/2002 | Lurie ............................ 514/561 |
| 6,527,716 B1 | 3/2003 | Eppstein ...................... 600/309 |
| 6,635,274 B1 | 10/2003 | Masiz et al. .................. 424/449 |
| 6,735,470 B2 | 5/2004 | Henley et al. ................. 604/20 |
| 6,936,589 B2 * | 8/2005 | Naito ............................. 514/25 |
| 7,041,657 B2 | 5/2006 | Vournakis et al. ............ 514/62 |
| 7,041,677 B2 | 5/2006 | Cutler .......................... 514/312 |

(Continued)

FOREIGN PATENT DOCUMENTS

| EP | 1 621 192 A1 | 2/2006 | ........... A61K 31/192 |
|---|---|---|---|
| WO | WO 01/17498 A1 | 3/2001 | ............... A61K 7/48 |

(Continued)

OTHER PUBLICATIONS

Ibuprofen Sodium Salt Chemical Informational Sheet, Santa Cruz Biotech, http://www.scbt.com/datasheet-252898-iburpofen-sodium-salt.html, obtained Aug. 7, 2013.*
European Patent Office—Authorized Officer Mathilde Ceyte, International Search Report and Written Opinion; PCT/US2009/057916; Feb. 1, 2010.
Baumler et al., "Q-Switch Laser and Tattoo Pigments: First Results of the Chemical and Photophysical Analysis of 41 Compounds," *Lasers in Surgery and Medicine*, vol. 26, pp. 13-21 (2003).
Bernstein, "Laser treatment of tattoos," *Clinics in Dermatology*, Dept. of Dermatology, Univ. of Penn. School of Med., Phil, PA, vol. 24, No. 1, pp. 43-55 (Jan. 2006).
Christensen et al., "The ultrastructure of tattoo marks," *Acta Pathol. Microbiol. Scand. [A]*, vol. 80, No. 4, pp. 573-576 (1972).
Elsaie et al., "Topical imiquimod in conjunction with Nd: YAG laser for tattoo removal," *Lasers Med. Sci.*, vol. 24, No. 6, pp. 871-875 (2009).

(Continued)

*Primary Examiner* — Jeffrey S Lundgren
*Assistant Examiner* — Meghan Finn
(74) *Attorney, Agent, or Firm* — Sunstein Kann Murphy & Timbers LLP

(57) ABSTRACT

A formulation and method for delivery of bioactive substances when applied to, or within, the skin or other exterior region of a mammal. for example, a patient, includes a vasoactive agent; an osmolyte; and an active ingredient. The formulation is sufficiently hygroscopic so as to create a condition of hypertonicity when absorbed by the skin. When the formulation is applied to the skin, the vasoactive agent can be delivered to the dermis so as to contact the vasculature of a patient.

73 Claims, 1 Drawing Sheet

(56) References Cited

U.S. PATENT DOCUMENTS

| | | | | |
|---|---|---|---|---|
| 7,069,073 | B2 | 6/2006 | Henley et al. | 604/20 |
| 7,105,172 | B1 | 9/2006 | Bolla | 424/400 |
| 7,115,588 | B2 | 10/2006 | Vournakis et al. | 514/62 |
| 7,179,253 | B2 | 2/2007 | Graham et al. | 606/9 |
| 7,179,789 | B2 | 2/2007 | Patt | 514/6 |
| 7,192,616 | B2 | 3/2007 | Cals-Grierson et al. | 424/769 |
| 7,604,797 | B2 | 10/2009 | Hicks | 424/78.06 |
| 2002/0147156 | A1* | 10/2002 | Petit et al. | 514/23 |
| 2003/0091659 | A1 | 5/2003 | Lu et al. | 424/727 |
| 2003/0104043 | A1 | 6/2003 | Brown et al. | 424/450 |
| 2003/0206946 | A1* | 11/2003 | Chung | 424/450 |
| 2004/0181211 | A1 | 9/2004 | Graham et al. | 606/9 |
| 2005/0042270 | A1* | 2/2005 | Aldred | 424/449 |
| 2005/0256204 | A1 | 11/2005 | Bitter, Sr. | 514/649 |
| 2005/0271596 | A1 | 12/2005 | Friedman et al. | 424/45 |
| 2006/0013769 | A1* | 1/2006 | Carter et al. | 424/9.1 |
| 2006/0013866 | A1* | 1/2006 | Carter et al. | 424/449 |
| 2006/0057081 | A1 | 3/2006 | Boxrud | 424/59 |
| 2006/0062836 | A1 | 3/2006 | Carter et al. | 424/449 |
| 2006/0217690 | A1 | 9/2006 | Bastin et al. | 606/9 |
| 2007/0078448 | A1 | 4/2007 | Lipman | 606/9 |
| 2007/0166252 | A1 | 7/2007 | Hattendorf et al. | 424/62 |
| 2007/0178121 | A1 | 8/2007 | First et al. | 424/239.1 |
| 2008/0044439 | A1 | 2/2008 | David | 424/239.1 |
| 2008/0112909 | A1 | 5/2008 | Faler et al. | 424/61 |
| 2008/0312296 | A1 | 12/2008 | Carter et al. | 514/356 |
| 2009/0053290 | A1 | 2/2009 | Sand et al. | 424/449 |
| 2009/0111770 | A1* | 4/2009 | Holzer et al. | 514/54 |
| 2009/0123570 | A1* | 5/2009 | Warner et al. | 424/677 |
| 2009/0221536 | A1 | 9/2009 | Fossel | 514/162 |
| 2010/0003353 | A1 | 1/2010 | Stephens et al. | 424/744 |
| 2010/0076035 | A1 | 3/2010 | Carter et al. | 514/365 |
| 2010/0145256 | A1 | 6/2010 | Carter et al. | 604/20 |
| 2010/0215632 | A1* | 8/2010 | Boss et al. | 424/94.1 |

FOREIGN PATENT DOCUMENTS

| | | | | |
|---|---|---|---|---|
| WO | WO 02/22120 A1 | 3/2002 | | A61K 31/275 |
| WO | WO 03/076600 A2 | 9/2003 | | C12N 5/00 |
| WO | WO 03/076600 A3 | 9/2003 | | C12N 5/06 |
| WO | WO 2005/051365 A1 | 6/2005 | | A61K 9/70 |
| WO | WO 2005/091891 | 10/2005 | | |
| WO | WO 2005/102282 | 11/2005 | | A61K 9/14 |
| WO | WO 2005/123190 | 12/2005 | | A61N 7/00 |
| WO | WO 2006/104660 | 10/2006 | | A61L 15/30 |
| WO | WO 2007/086395 A1 | 8/2007 | | A61K 361/165 |
| WO | WO 2007/103555 | 9/2007 | | A61K 8/49 |
| WO | WO 2008/054059 A1 | 5/2008 | | A61K 31/35 |
| WO | WO 2008/109124 A1 | 9/2008 | | A61K 31/21 |
| WO | WO 2008/156758 A1 | 12/2008 | | A61K 31/74 |
| WO | WO 2009/111075 | 9/2009 | | A61N 5/06 |

OTHER PUBLICATIONS

Ferguson et al., "The Q-switched neodymium: YAG laser and Tattoos: a microscopic analysis of later-tattoo interactions," *British Journal of Dermatology*, vol. 137, pp. 405-410 (1997).

Ferndale Pharmaceuticals Ltd., "LMX-4 lidocaine 4% w/w/ cream", *Summary of Product Characteristics*, URL: http://www.lmx4.co.uk/PDF/LMX4_SPC, 5 pages (Nov. 2007).

Goldberg, "Laser Treatment of Vascular Lesions," *Clinics in Plastic Surgery*, vol. 27, No. 2, pp. 173-180 (2000).

Jumaa et al., "In vitro investigation of the effect of various isotonic substances in parenteral emulsions of human erythrocytes," *Euro. J. Pharm. Sci.*, vol. 9, pp. 207-212 (1999).

Kautz et al., "Management of Rosacea with Intense Pulsed Light (IPL) Systems and Laser," *Medical Laser Application*, vol. 23, No. 2, pp. 65-70 (2008).

Kilmer et al., "Clinical Use of the Q-switched Ruby and the Q-Switched Nd: YAG (1064 nm and 532 nm) lasers for treatment of tattoos," *J. Dermatol. Surg. Oncol.*, vol. 19, No. 4, pp. 330-338 (1993).

Lea et al., "Human tattoo. Electron microscopic assessment of epidermis, epidermal-dermal junction, and dermis," *J. Dermatol.*, vol. 26, No. 7, pp. 453-458 (1987).

MacKenzie et al., "Three-Generation Reproduction Study of Rats Ingesting Up to 100% Sorbitol in the Diet—and a Brief Review of the Toxicological Status of Sorbitol," *Fd. Chem. Toxic*, vol. 24, No. 3, pp. 191-200 (1986).

McGill et al., "The Effect of Ambient Temperature on Capillary Vascular Malformations," *Br. J. Dermatol.*, vol. 154, No. 5, pp. 896-903 (2006).

Nase et al., "The Latest Advances in Rosacea Treatment: Triple-Pass Laser Treatment," *Dermatology Times* (Updated: Jun. 2005) http://www.drnase.com/rosacea_photoderm.htm.

Nette et al., "Specific effect of the infusion of glucose on blood volume during haemodialysis," *Nephrol. Dial Transplant*, vol. 17, pp. 1275-1280 (2002).

Newton et al., "Mechanisms influencing the vasoactive effects of lidocaine in human skin," *Anaesthesia*, vol. 62, No. 2, pp. 146-150 (Dec. 2006).

Ricotti et al., "Laser-assisted tattoo removal with topical 5% imiquimod cream," *Dermatol Surg.*, vol. 33, No. 9, pp. 1082-1091 (2007).

Svaasand et al., "Increase of dermal blood volume fraction reduces the threshold for laser-induced purpura: Implications for port wine stain laser treatment," *Lasers in Surgery and Medicine*, vol. 34, No. 2, pp. 182-188 (Feb. 1988).

Solis et al., "Experimental Nonsurgical Tattoo Removal in a Guinea Pig Model with Topical Imiquimod and Tretinion," *Dermatol. Surg.*, vol. 28, pp. 83-87 (2002).

Taylor et al., "Light and electron microscopic analysis of tattoos treated by Q-switched ruby laser," *J. Invest. Dermatol.*, vol. 97, No. 1, pp. 131-136 (1991).

Uedo et al., "Measurement of Carcinoembryonic Antigen in Colonic Effluent as a High-Risk Marker for Colorectal Carcinoma," *Cancer Detection and Prevention*, vol. 24, No. 3, pp. 290-294 (2000).

Wheeland, "Clinical Uses of Lasers in Dermatology," *Lasers in Surgery and Medicine*, vol. 16, No. 1, pp. 2-23 (1995).

WiseAcre Gardens, Bugleweed—Perennials: *Ajuga reptans*, Found at: html://www.wiseacre-gardens.com/plants/perennial/bugleweed.com.

Zelickson et al., "Clinical, Histologic, and Ultrastructural Evaluation of Tattoos Treated with Three Laser Systems," *Lasers in Surgery and Medicine*, vol. 15, No. 4, pp. 364-372 (1994).

European Patent Office, *EPO Communication pursuant to Rules 161(1) and 162 EPC*—Application No. EP 09764427.2, dated Nov. 21, 2011 (2 pages).

Schlich LLP, *Response* dated Jun. 1, 2012, pertaining to EPO Communication under Rules 161(1) and 162 EPC—Application No. EP 09764427.2 (4 pages).

The International Bureau of WIPO, *International Search Report*—International Application No. PCT/US2009/047098, dated Aug. 27, 2009, together with the Written Opinion of the International Searching Authority (10 pages).

The International Bureau of WIPO, *International Search Report*—International Application No. PCT/US2009/066865, dated Jul. 15, 2011, together with the Written Opinion of the International Searching Authority (15 pages).

The International Bureau of WIPO, *International Preliminary Report on Patentability*—International Application No. PCT/US2009/066865, dated Sep. 20, 2011 (8 pages).

United States Patent and Trademark Office, *Office Action*, dated Mar. 7, 2012, pertaining to U.S. Appl. No. 12/631,698, 35 pages.

Nancy C. Wilker, Ph.D., Esq. Sunstein Kann Murphy & Timbers LLP, *Response*, filed May 23, 2012, pertaining to U.S. Appl. No. 12/631,698, 39 pages.

United States Patent and Trademark Office, *Office Action*, dated Sep. 7, 2012, pertaining to U.S. Appl. No. 12/631,698, 18 pages.

Nancy C. Wilker, Ph.D., Esq. Sunstein Kann Murphy & Timbers LLP, *Request for Continued Examination Along with Response*, filed Dec. 7, 2012, pertaining to U.S. Appl. No. 12/631,698, 11 pages.

Canadian Intellectual Property Office, *Voluntary Amendment*, dated Jan. 12, 2011, pertaining to Application No. 2,702,604 (2 pages).

(56) References Cited

OTHER PUBLICATIONS

Canadian Intellectual Property Office, *Official Action*, dated Mar. 9, 2012, pertaining to Application No. 2,702,604 (12 pages).
Gowling LaFleur Henderson LLP, *Response to Official Action*, dated Sep. 6, 2012, pertaining to Application No. 2,702,604 (25 pages).
Castillo Grau & Associates, *Substantive Examination Results*, pertaining to Application No. 11 045.145, dated Nov. 19, 2012, 7 pages.
Instituto Mexicano de al Propiedad Industrial, Office Action dated Jul. 7, 2015, Application No. MX/a/2010/004169, 3 pages.
Instituto Mexicano de al Propiedad Industrial [English Translation], Office Action dated Jul. 7, 2015, Application No. MX/a/2010/004169, 3 pages.

* cited by examiner

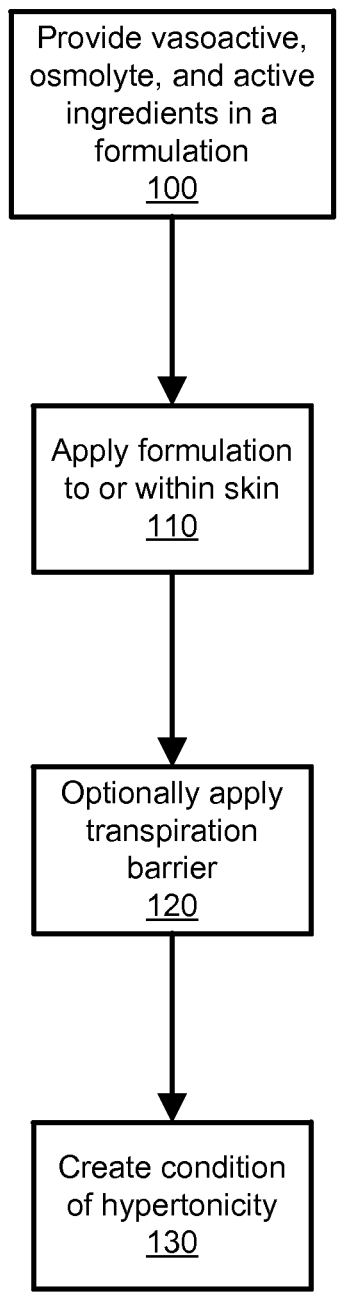

TRANSDERMAL DRUG DELIVERY USING AN OSMOLYTE AND VASOACTIVE AGENT

CROSS-REFERENCE TO RELATED APPLICATION

This application for United States patent claims the benefit of U.S. Provisional Patent Application Ser. No. 61/099,129, filed on Sep. 22, 2008, which is hereby incorporated herein by reference.

TECHNICAL FIELD

The present invention relates to methods and compositions for delivering bioactive substances to and/or via the skin.

BACKGROUND

Transdermal drug delivery is a highly attractive mode for reasons that include patient convenience, compliance and comfort, avoidance of irritation to the gastrointestinal tract, bypass of hepatic and gastrointestinal metabolism, and reduction of fluctuations in drug plasma. However, a key challenge in transdermal drug delivery is the penetration of several barriers in the skin and underlying tissues to achieve systemic or localized drug deposition.

If transdermal delivery is desired, the first barrier to overcome is the outer layer of the skin, the epidermis. The outer layer of skin is made up of living and dead epithelial cells that are made in the stratum basale and are continually pushed to the surface as new cells are made. The cells are initially alive but eventually metabolism ceases and the cells undergo programmed death becoming flattened and keratinized. These dead cells create the outermost layer of the epidermis, the stratum corneum. It is the stratum corneum that is the principal barrier to the percutaneous penetration of topically applied drugs.

The dermis is the layer of skin beneath the epidermis and is separated from the epidermis by a basement membrane. The dermis consists mainly of connective tissue; nerve endings; sweat, sebaceous, and apocrine glands; hair follicles; and blood vessels. The blood vessels in the dermis release plasma containing water, nutrients and oxygen into the interstitial spaces and channels of the epidermis and dermis to provide nourishment to these tissues and, in a separate but continuous action, re-absorb interstitial fluid back into the capillaries and lymphatic vessels thereby removing cellular waste products and water.

SUMMARY OF THE INVENTION

In an illustrative embodiment of the present invention, there is a formulation for delivery of bioactive substances to a patient via a site of application on an external region of the patient. The formulation includes a vasoactive agent, an osmolyte, and an active ingredient. The formulation is sufficiently hygroscopic to create a condition of hypertonicity when absorbed by at the site of application. When the formulation is applied, the vasoactive agent causes an increased flow of blood in the skin.

In related embodiments, the increase in blood flow can be greater than 1%, or greater than 5% as measured by laser-Doppler velocimetry. The osmolyte can be absorbed by the skin and the increased blood flow can work in synergy with the osmolyte to enhance penetration of the active ingredient.

The vasoactive agent can be a vasodilator in an amount effective to cause increased permeation of fluid through the walls of blood vessels in the skin of the patient. The vasoactive agent can be a vasoconstrictor in an amount effective to cause decreased blood flow through an affected vasculature and to cause decreased permeation of fluid through the walls of blood vessels in the skin of the patient. The formulation can cause the vasoactive agent to pass through a basement membrane of the skin.

The vasoactive agent and the osmolyte can exert a synergistic physiological change in the skin of a patient to thereby allow transport of the active agent through the skin. The vasoactive agent and the osmolyte can exert a synergistic physiological change in the skin of a patient to thereby allow transport of the active agent into the epidermis, into the dermis, or into systemic circulation.

The formulation can include a moisture resisting transpiration barrier. The moisture resistant transpiration barrier may include at least one of a chemical barrier and a physical barrier. Both a chemical barrier and a physical barrier can be used, together or sequentially. The formulation may be packaged in a water-resistant container.

The formulation may further include a penetration enhancer. The vasoactive agent can be a moiety of a bifunctional molecule that combines vasoactive and penetration enhancing properties.

The formulation can include an excipient, and may be incorporated into a drug administration patch.

The active ingredient can be a sirtuin inhibit or a sirtuin activator. The vasoactive agent can include methyl nicotinate.

In an embodiment, a method for enhancing penetration of an active ingredient through the skin or other exterior tissue of a patient includes applying the above-formulation. The method may include working the skin; for example, massaging, using iontophoresis, using sonophoresis, or using a microneedle. An initial transpiration barrier can be applied to a region of the skin and removed prior to application of the formulation to the region. The application can be topical.

A method for enhancing the penetration of an active ingredient into or through the skin includes introducing the active ingredient with a vasoactive agent and an osmolyte into or onto a region of the skin to cause the active agent to cross the basement membrane.

The active ingredient can penetrate into the epidermis, dermis, subcutaneous regions, or systemic circulation. The vasoactive agent, the osmolyte, and the active ingredient can be included in a formulation that is sufficiently hygroscopic to create a condition of hypertonicity in the skin.

The active ingredient can be a sirtuin inhibitor or sirtuin activator and the region of the skin can be selected from a basal cell carcinoma, melanoma, cervical carcinoma, cervical condyloma, genital wart, herpetic lesion, diabetic neuropathy, chemotherapy-derived neuropathy, general neuropathy, solid tumor, psoriasis, and eczema.

In accordance with another illustrative embodiment, a method for topical delivery of a active ingredient to a patient at a topical site of application includes administering a vasoactive agent to the site of application, administering an osmolyte to the site of application, and administering an active ingredient to the site of application, wherein the osmolyte is in an amount sufficient to create a condition of hypertonicity when absorbed at the site of application and the vasoactive agent the vasoactive agent causes an increased flow of blood in the skin.

In related embodiments, the vasoactive agent and osmolyte and active ingredient can be applied sequentially. Alternately, the vasoactive agent and osmolyte are applied together. The method may also feature applying a transpiration barrier to the site of application.

In another embodiment, a kit is used for topical delivery of an active ingredient to a patient. The kit includes a vasoactive agent, an osmolyte, an active ingredient; and a set of written instructions for use, by or on said patient, of said vasoactive agent, said osmolyte, and said active ingredient according to the method of topical delivery.

In another embodiment, a kit for topical delivery of an active ingredient to a patient includes a vasoactive agent, an osmolyte, an active ingredient, an occlusive barrier; and a set of written instructions for use, by or on the patient, of the vasoactive agent, osmolyte, and active ingredient according to the method of topical delivery.

In another embodiment, there is a method of manufacturing a medicament for transdermal administration. The method includes combining a vasoactive agent; an osmolyte; and an active ingredient in sufficient amounts to cause permeation of the active ingredient to at least one affected region of a patient when applied to one of the skin and other exterior region of the patient.

BRIEF DESCRIPTION OF THE DRAWINGS

The foregoing features of the invention will be more readily understood by reference to the following detailed description, taken with reference to the accompanying drawings, in which:

FIG. 1 is a flow diagram showing a method for transdermal drug delivery in accordance with an embodiment of the invention.

DETAILED DESCRIPTION OF SPECIFIC EMBODIMENTS

Definitions. As used in this description and the accompanying claims, the following terms shall have the meanings indicated, unless the context otherwise requires:

A "formulation" is a preparation in which various chemical substances are combined with an active ingredient. As used herein, a formulation includes a composition of the invention in the form of an ointment, cream, lotion, gel, salve or the like, for topical application or delivery of the drug to a patient. In some embodiments, as appropriate, a formulation is used in conjunction with a delivery system (such as a patch) impregnated with or containing a composition suitable for topical application.

A "transpiration barrier" shall mean a component such as a solid patch, a hydrophobic chemical component, or a self-assembling chemical component (including components that form gels) that is capable of preventing water loss from skin tissue due to transpiration when applied to the skin of a patient.

An "osmolyte" shall mean a molecule having an affinity for water (i.e., hydrophilicity or hygroscopicity) to thereby draw water from cells, vasculature or other structures of the skin.

A "penetration enhancer" shall mean a compound, particle, or other substance or material that when included in a formulation that also includes a vasoactive agent and is applied topically to the skin, increases the rate or amount of transport of an active ingredient past the epidermis of the skin. An osmolyte can be a penetration enhancer, but a penetration enhancer need not be an osmolyte.

"Topical" shall mean application of a formula to body surfaces such as the skin or mucous membranes, for example the vagina, anus, throat, eyes and ears. For purposes of applying a formula, topical application shall include application to the stratum corneum, microinjection to the epidermis (such as can be achieved with microneedles), or use of sonophoresis, iontophoresis or other permeation-enhancing methods, without piercing of the basement membrane and subsequent injection to the dermis or subcutaneous structures.

In connection with a component of a formulation or an entire formulation, "hygroscopic" shall mean a degree of hydrophilicity of that portion of the formulation that enters the skin when applied. Hygroscopic components of a formulation will tend to absorb water from their environment. The term shall be applicable to solution-phase, emulsion-phase and solid particles. The term shall be applicable to not only osmolytes but to other components of a formulation. Hydrophilicity can be measured by a partition coefficient between water and a less polar solvent such as chloroform.

An "active ingredient" shall mean any component of a formulation that provides pharmacological activity or other direct effect in the diagnosis, cure, mitigation, treatment, or prevention of disease. As non-limiting examples of active ingredients that are useful in the topically applied pharmaceutical formulations and methods of the instant invention there may be mentioned: antifungal agents; anti-inflammatory agents, such as non-steroidal anti-inflammatory drugs (NSAIDS) and steroidal anti-inflammatory drugs; antibiotics; antiviral agents; anti-neoplastic agents; astringents; anesthetics; systemic drugs; steroid hormones, such as estradiol and testosterone; cosmetic agents, such as skin moisturizers, protectants, and emollients; nutrients, such as vitamins; and ceramides, and other known to those skilled in the art (e.g., those ingredients listed by the U.S. Food and Drug Agency in "Approved Drug Products with Therapeutic Equivalence Evaluations (Orange Book)", available at: http://www.fda.gov/Drugs/InformationOnDrugs/ucm129662.htm that are judged suitable by those skilled in the art). Preferably, the active ingredient is capable of inducing a desired physiological effect on a targeted skin or other tissue other than solely a vasodilatory or vasoconstrictory effect.

A "vasoactive agent" shall include either a vasodilator or a vasoconstrictor component of a formulation, and includes pro-drugs of such components.

"Patient" shall mean any animal, including mammals such as a human, non-human primate, mouse, rat, guinea pig, rabbit, pig, horse or dog.

In accordance with illustrative embodiments of the present invention, a formulation includes a vasoactive agent and an osmolyte that can work together in an additive or synergistic manner to enable penetration of an active agent into the skin (epidermis or dermis) or through the skin and into general systemic blood circulation thereby to exert a local or systemic therapeutic effect, respectively. Optionally, a transpiration barrier, penetration enhancer, or both can increase the effectiveness of the penetration, also in an additive or synergistic manner. As a result of using such formulations, an expanded range of candidate transdermal active ingredients can be used. For example, by using such formulations, higher molecular weight and less hydrophobic active agents can penetrate the epithelial tissue. In an illustrative embodiment, the formulation is applied to the skin and the vasoactive agent is delivered to the dermis. As a result, the vasoactive agent contacts the cutaneous vasculature. As a result of contact with the vasculature, the vasoactive agent can increase blood flow in the skin (e.g. by greater than 1%, 5% or 10%). The increase in blood flow can be measured relative to blood flow prior to treatment with the formulation or relative to blood flow in skin treated with a control formulation lacking the vasoactive agent. The increased blood flow can be measured using laser Doppler velocimetry, which typically outputs a voltage that is proportional to the velocity of cells moving through the blood. Together with osmotic effects of the osmolyte on the tonicity of the skin, this increased blood flow can enhance the penetration of an active ingredient into or through the skin. In a further illustrative embodiment, such formulations are used to enhance the uptake of anti-neoplastic active ingredients into a skin lesion or tumor. The anti-neoplastic active ingredient can, for example, act on the sirtuin pathway.

FIG. 1 is a flow diagram, which outlines steps of a method for causing an active agent to penetrate the skin, thereby entering the epidermis, dermis, and optionally the systemic circulation. The active ingredient is combined in a formulation with a vasoactive agent (a vasodilator or vasoconstrictor) and an osmolyte (step 100). Optionally, the formulation can include excipients, penetration enhancers, lipids, or other substances. The formulation can also be a patch or a component of a patch or similar drug delivery device.

The formulation can be applied to the skin; i.e., topically (step 110). For example, the formulation can be a cream, lotion, ointment, gel, or other substance suitable for topical application to the skin. Optionally, the skin can be mechanically worked to enhance the penetration of the active ingredient past the epidermis (e.g., into or through the basement membrane). For example, mechanical work can be used in the form of massaging, or sonophoresis. Mechanical working processes also include processes of cutting, ulceration, wound formation or piercing. For example, piercing the skin with microneedles (e.g., with a device having projections designed to pierce the stratum corneum without the substantial triggering of deeper pain receptors) can aid in the drug delivery process. Microneedles are disclosed, for example, in U.S. Pat. No. 6,611,707, issued on Aug. 26, 2003 to Prausnitz, which is incorporated herein by reference in its entirety. Sonophoresis (e.g., via ultrasound) can also be used to exert mechanical work and enhance penetration. Electrical work can also be employed; e.g., iontophoresis. The above list is an illustrative and not exhaustive list of working processes that can be employed in connection with embodiments of the present invention.

Optionally, the formulation can be delivered into the skin. For example, the formulation can be injected into the epidermis with microneedles.

In an illustrative embodiment, the method includes optionally applying a transpiration barrier (step 120). The transpiration barrier can be a water impermeable drug administration patch; for example, a sheet of water-resistant plastic with an adhesive layer or other attachment mechanism. The patch can be applied atop a formulation applied to the skin. Alternately, the patch can be impregnated with the formulation and applied to the skin to contact the vasoactive agent, active ingredient, and osmolyte with the skin while forming the transpiration barrier. A water-impermeable wrap, glove, sock, mitten, or the like can also serve to create a physical barrier. Alternately, or in addition, the transpiration barrier can include a molecular (i.e., chemical) barrier; i.e., one that contains a plurality of molecules or particles that are at least initially unbonded and which dry on or embed in the skin to produce a moisture-resistant barrier. For example, the molecular barrier can include silicone, titanium oxide, polyvinyl alcohol and hydrogels. It should be noted that both a chemical barrier and a physical barrier can be used together or sequentially. In another embodiment, a water-resistant patch is applied to the skin for a period (e.g., 0.5 to 60 minutes) prior to removal of the patch and application of a formula described herein.

By including, in the formulation, a suitable osmolyte (e.g., a salt or a sugar) at a high enough concentration, a condition of hypertonicity can be created in the skin or other external body region to which the formulation is applied (step 130). The hypertonic condition can include an elevated osmotic pressure in the extracellular milieu as compared to the intracellular cytoplasm of the skin cells. This condition of hypertonicity can work cooperatively or synergistically with the vasoactive agent to enhance delivery of the active compound into the epidermis, or through the basement membrane to the dermis or other skin structures. In some cases, compound entering the epidermis can enter the systemic circulation. Without wanting to be bound by any particular mechanistic hypothesis, the hypertonic condition can cause crenation of cells in the skin, which can widen extracellular channels in the skin, or open new channels. The vasoactive agent can act on the microvasculature within the dermis to generate a vasodilation event that releases plasma and/or interstitial fluid into the intercellular spaces surrounding the vessel and into the dermis and epidermis. If a transpiration barrier is used, the pressure created by the released plasma can build at the impermeable transpiration barrier to create a second osmotic pressure event based on water influx from the vasculature. The first osmotic event with the presence of an osmolyte is a subtle crenating process that can open up the epithelium for better drug and particle movement. The second osmotic event is the creation of a bolus-type gradient of osmotic pressure in the localized skin tissue due to the presence of excessive amounts of interstitial fluid released from the microvasculature by the vasodilator with no place to go except to be re-directed back into the body. The osmotic modifying agents continue to exert their effect on cells as they move through the epidermis, compounding or synergizing the effect of the vasodilating modifying agent on the movement of the drug molecules within the epidermis and the dermis. The combination of the vasodilating and osmotic modifying agents can generate a larger gradient than osmotic pressure generated from the epidermal cell water movement alone and can induce greater physical space between the epithelial cells in which drug molecules can move. This combined and elevated osmotic pressure can continue to drive the active drug ingredient through the basement membrane and into the dermis to deliver the active agent to local dermal or subcutaneous tissues or to the lymph and blood capillaries for systemic distribution.

Although convenient, it may not be necessary to include all of the aforementioned components of the formulation in a single composition—the vasoactive agent, active ingredient and osmolyte can be applied sequentially and in various orders so long as the ultimate result is to combine the three types of molecules in the skin at sufficient concentration to effect penetration of the active agent to therapeutically effective levels. A transpiration barrier can also be applied sequentially with respect to the other components one or more times.

Examples of osmolytes include one or more monosaccharides (e.g., glucose, fructose, galactose, as glucose, fructose, galactose, ribose, rhamnose, and xylopyranose, disaccharides (e.g., sucrose, lactose, maltose, trehalose, cellobiose, gentiobiose, isomaltose, kojibiose, laminaribiose, mannobiose, melibiose, nigerose, rutinose and xylobiose), and ions (e.g., divalent and monovalent ions such as lithium, sodium, potassium, rubidium, cesium, beryllium, magnesium, calcium, iodine, strontium and barium ions). The ionic portion of the formulation can comprise a salt, such as sodium chloride.

In an embodiment, the osmolytes can be included in the formulation in sufficient concentration (and therefore at sufficient activity) to create a condition of local hypertonicity in the skin. For example, the osmolarity of the formulation can be greater than 290 milliosmol/L and can result in greater than 290 milliosmol/L inside the skin. In an embodiment, the osmolarity of the formulation is substantially greater than 290 milliosmol/L; for example: 350, 600, or 900 milliosmol/L.

In embodiments, the formulation is packaged in a water resistant container due to its hygroscopic nature.

The vascular modifying agent can be a vasodilator. The vasodilator can be in an amount that is effective to cause increased permeation of fluid through the walls of blood vessels in the skin of the patient. Examples of vasodilators include amrinone, arginine, bamethan sulphate, bencyclane fumarate, benfurodil hemisuccinate, benzyl nicotinate, buflomedil hydrochloride, buphenine hydrochloride, butalamine hydrochloride, cetiedil citrate, ciclonicate, cinepazide maleate, cyclandelate, di isopropylammonium dichloroacetate, ethyl nicotinate, hepronicate, hexyl nicotinate, ifenprodil tartrate, inositol nicotinate, isoxsuprine hydrochloride, kallidinogenase, methyl nicotinate, naftidrofuryl oxalate, nicametate citrate, niceritrol, nicoboxil, nicofuranose, nicotinyl alcohol, nicotinyl alcohol tartrate, nitric oxide, nonivamide, oxpentifylline, papaverine, papaveroline, pentifylline, peroxynitrite, pinacidil, pipratecol, propentofyltine, raubasine, suloctidil, teasuprine, thymoxamine hydrochloride, tocopherol nicotinate, tolazoline, xanthinol nicotinate, diazoxide, hydralazine, minoxidil, and sodium nitroprusside. Centrally acting agents include clonidine, quanaberz, and methyl dopa. Alpha adrenoceptor blocking agents include indoramin, phenoxybenzamine, phentolamine, and prazosin. Adrenergic neuron blocking agents include bedmidine, debrisoquine, and guanethidine. ACE inhibitors include benazepril, captopril, cilazapril, enalapril, fosinopril, lisinopril, perindopril, quinapril, and ramipril. Ganglion blocking agents include pentolinium and trimetaphan. Calcium channel blockers include amlodipine, diltiazem, felodipine, isradipine, nicardipine, nifedipine, nimodipine, and verapamil. Prostaglandins including: prostacyclin, thrombuxane A2, leukotrienes, PGA, PGA1, PGA2, PGE1, PGE2, PGD, PGG, and PGH. Angiotensin II analogs include saralasin. Other suitable vasodilators include nitroglycerin, labetalol, thrazide, isosorbide dinitrate, pentaerythritol tetranitrate, digitalis, hydralazine, diazoxide, and sodium nitroprusside, derivatives of these and combinations of the foregoing.

The vasodilator (or mixture of vasodilators) in the formulation can be chosen from the classes of endothelium-dependent vasodilators, endothelium-independent vasodilators and prostaglandin-based vasodilators to elicit the production of endogenous prostaglandins. Prodrugs of any of the foregoing vasodilators can also be used. In an embodiment, inclusion of the vasodilator in the formulation will relax or dilate the dermal arteries and arterioles and therefore increase the volume of blood flow into the capillary network. This increased volume of blood will subsequently result in an increased trans-capillary flux of water from the vessel into the surrounding tissue, including the epidermis. Other examples of vasodilators include nitroglycerine, arginine and some arginine derivatives, acetylcholine, sodium nitroprusside, methyl nicotinate, hexyl nicotinate, arachidonic acid, prostaglandin $D_2$, prostaglandin $I_2$, tolazoline, papaverine. Arginine is a known substrate for nitric oxide synthase and it is known that nitric oxide can exert a vasodilatory effect. However, it is believed that arginine is unable to penetrate to the dermis when applied topically.

In an embodiment, the vasodilator is methyl nicotinate at a concentration of 0.05% by weight, or more. Methyl nicotinate is known to act via the prostaglandin $D_2$ pathway Optionally, the methyl nicotinate is combined with a second vasodilator, such as a vasodilator that acts via the endothelial dependent pathway (e.g., acetylcholine).

Alternately, the vascular modifying agents can be vasoconstrictors. Examples of vasoconstrictors include adenosine triphosphate, amphetamine, antazoline, asymmetric dimethylarginine, cocaine, dopamine, endothelin, ephedrine, epinephrine, ergine, hydroxyamphetamine, isoproterenol, levonordefrin, metaraminol, methamphetamine, methoxamine, methylphenidate, neuropeptide Y, naphazoline, norepinephrine, oxymetazoline, phenylephrine, pseudoephedrine, tetrahydozoline, thromboxane, tramazoline, tyramine, derivatives of these and combinations of the foregoing.

The vasoactive agent can be chosen to exert effects rapidly (e.g., within 10 minutes or less), over a longer period of time (e.g., over the course of an hour or more). The vasoactive agent can also be chosen to give a delayed release (e.g., release begins after 10 minutes). Multiple vasoactive agents can be combined to result in both rapid and longer-term effects on the skin.

Examples of active ingredients include acetaminophen, acetohydoxamic acid, acetophenazine, acyclovir, albuterol, allopurinol, amiloride, amoxicillin, amphetamine, ampicillin, antisense polymers, atenolol, baclofen, beclomethasone, benfotiamine, betamethasone, budesonide, bumetanide, butorphanol, carbamazepine, carphenazine, cefuroxime, cephradine, chloramphenicol, chlorothiazide, chlorzoxazone, cinoxacin, clorazepate, cloxacillin, cyclacillin, dapsone, dicloxacillin, diethylstilbestrol, dopamine, doxorubicin, erythropoietin, estradiol, fenoprofen, human growth hormone, hydralazine, hydrochlorothiazide, ibuprofen, indomethacin, insulin, isoproterenol, levodopa, levothyroxine, meclofenamate, melphalan, metformin methyl salicylate, metronidazole, minoxidil, morphine, nadolol, nalidixic acid, naproxen, nomifensine, norfloxacin, oxaprozin, paramethasone, peptide fragments, perphenazine, phenylpropanolamine, probenecid, quinethazone, ritodrine, scopolamine, serotonin, terbutaline, terfenadine, tocainide, triamterine, trimethoprim, valacyclovir and any derivatives of these and combinations of the foregoing.

The active ingredient can also be a sirtuin inhibitors such as nicotinamide, AIII, coumarin, sirtinol, alpha-NAD, carbamido-NAD, trichostatin A, suramin sodium, apicidin, BML-210, BML-266, depudecin, HC Toxin, ITSA1, nullscript, phenylbutyrate, sodium, scriptaid, splitomicin, or suberoyl bis-hydroxamic acid.

Further, the active ingredient can be sirtuin activators such as resveratrol, isonicotinamide, butein, or luteolin.

In some embodiments of the invention, the active ingredient comprises a biological agent. Examples of biological agents include as peptides, small proteins and protein fragments; antibody fragments; small nucleic acids and nucleic acid fragments such as aptamers and siRNA; or combinations of these.

As mentioned above, the formulation can include penetration enhancers. Examples of penetration enhancers include individual fatty acids, fatty acid esters, polyols, amides, various anionic, cationic and nonionic surfactants such as but not limited to sodium laurate and sodium lauryl sulfate, phospholipids, cholesterol and cholesterol derivatives, m-pyrrole, dimethyl acetamide, limonene, sphingolipids, ceramides, terpenes, alkanones, menthol, various organic acids, such as but not limited to salicylic acid, citric and succininc acid, prostaglandins, decyl methyl sulfoxide, urea, sulfoxide alcohols, plant extract oils. Suitable fatty acids include without limitation: linoleic acids, linolenic acids, oleic acids, stearic acids, and myristic acids. Phospholipids include without limitation: phosphatidylcholine, phosphatidylethanolamine, and phosphatidylserine. Plant extract oils include oils of peanut, hemp, borage, olive, sunflower, soybean, monoi and macadamia. The plant extract oil can be mixed with an alcohol such as ethyl alcohol, isopropyl alcohol, and methyl alcohol.

The formulation can also include excipients or carriers such as Stearyl Alcohol, Polysorbate 20, Caprylic/Capric Glyceride, Petrolatum, Beeswax, Lecithin, Dimethicone, Alkylmethyl Siloxane, Stearic Acid, Palmitic Acid, Lanolin, Linoleic Acid, Isopropyl Myristate, Stearyl Octanoate and Cetyl Octanoate, and Polysorbate 80.

Embodiments of the invention can be useful for medical conditions such as but not limited to basal cell carcinomas, melanoma, cervical carcinomas, cervical condylomas, genital warts, herpetic lesions, diabetic neuropathy, chemotherapy-derived neuropathy, general neuropathy, benign prostatic hypertrophy, solid tumors, psoriasis, and eczema. In some embodiments, the active ingredient is a sirtuin inhibitor or sirtuin activator and the formulation is applied to the skin of a patient to treat one of these medical conditions. Where accessible, the formulation can be applied to a region of the skin or tissue associated with the medical condition.

In some embodiments of the invention, the formulation is cosmetically suitable in that it can be applied to the skin without detrimentally affecting the appearance of the skin.

In addition to application to the skin, the formulation can be applied to other exterior regions of the body including to the fingernails, toenails, ocular tissue, vagina, rectum (as a suppository), and other tissue surfaces containing an epithelial cell layer.

In some embodiments, the functions of two or more vasoactive agents, osmotic agents, and optional penetration enhancers can be provided by a single compound. For example, a bi-functional molecule that combines vasodilation and penetration enhancing properties, such as described in United States Published Patent Application No. 2008/0312296, published Dec. 18, 2008, which is hereby incorporated by reference, can be combined with an osmotic agent and other ingredients as described herein.

In some embodiments, when the formulation is applied, the vasoactive agent is delivered to the dermis and contacts the vasculature of the patient. For example, the topical formulation can have a vasoactive agent (e.g., methyl nicotinate) and an osmolyte (e.g, a salt). When the formulation is applied topically to a region of the epidermis, the salt and optional transpiration barrier assist the vasoactive agent in crossing the epidermis and entering the dermis. In the dermis, the vasoactive agent acts on the micro circulatory system to increase blood flow in the skin. An increase or decrease in blood flow in the local dermis surrounding the area of formulation application will reflect the increased or decreased permeation of fluid through the blood vessels in the skin of the patient. As a result of the increased blood flow, and possibly in connection with the osmolyte and/or transpiration barrier, the active ingredient is transported into the dermis, and possibly into systemic circulation.

A formulation can be tested for its ability to increase circulation using laser Doppler velocimetry measurements. Such measurements are known in the art (see, e.g., Holloway G A Jr, Watkins D W., 1977, Laser Doppler measurement of cutaneous blood flow. J Invest Dermatol., September; 69(3):306-9). The test can be performed on participants after a 20-minute acclimatization period in a warm environment (room temperature 24° C.). For each subject, the blood flow response is measured with the non-invasive test before and after the application of the test formulation and at various intervals of time after the application until the blood flow has returned to a pre-application level. The measurement of skin blood flow can be evaluated using a Laser Doppler Perfusion Imager (LDPI Lisca 2.0, Lisca development AB, Linkoping, Sweden). This apparatus employs a 1 mW Helium-Neon laser beam of 633 nm wavelength, which sequentially scans the tested area. Typically, maximum number of measured spots is 4096 and the apparatus produces a color-coded image of the tissue perfusion distribution on a computer monitor. The data acquired from the instrument can be statistically analyzed with The Minitab statistical package (Minitab, State College, Pa.) for personal computers. For intra-group comparisons, the paired t-test can be used to compare changes between baseline and the maximal vasodilation. The test can be used for comparison between the two groups of patients. Changes in the microvascular blood flow can be expressed as the difference between the peak response and the baseline blood flow (e.g., in ml/min, laser-doppler velocimetry voltage readout, or other suitable units).

In some embodiments of the invention, application of the formulation can cause an increase in blood flow at or near the region of application. The increase can be greater than or equal to 1%, 5%, 10%, or more.

Animal models can be used to evaluate the effectiveness of a topically applied formulation in penetrating the skin tissue for either intradermal or transdermal systemic distribution of the active ingredient. Animal models that are preferred include pigs, guinea pigs, rabbit and mini-pigs. An example of the procedure used for such a study using guinea pigs is as follows: Male Hartley guinea pigs (250-300 g) are shaved on the back, and an area of 4×4 cm depilated with Nair® depilatory cream. After approximately 24 hours, 0.5 g of test compound in a topical formulation is applied to the 4×4 cm area and covered with an occlusive wrap. At 1, 2, 4, 8 and 24 hours after application, groups of >5 animals are anesthetized with isoflurane, the application area is swabbed with alcohol, blood is removed by cardiac stick, and the skin tissue of the application area is excised. One group of animals is anesthetized and blood and skin tissue are removed as vehicle control. Blood samples are processed to serum and analyzed for the presence of an active ingredient via HPLC. The skin below the area of compound application on each animal group is excised, weighed, homogenized in a mixture of acetonitrile and 0.1N HCl (50:50 v/v), centrifuged, and the extract analyzed for the presence of active ingredient via HPLC via HPLC. The amount of active ingredient in the blood and the amount of active ingredient in the skin tissue may be compared to give information about the pharmacokinetics of the active ingredient. For delivery to skin tissue (e.g., a skin tumor or lesion), a higher amount in the skin relative to the blood is more efficacious, whereas when the goal is systemic delivery of the active ingredient, a higher distribution in the blood is more efficacious.

In another embodiment, a kit is used for topical delivery of an active ingredient to a patient. The kit includes a vasoactive agent, an osmolyte, an active ingredient; and a set of written instructions for use, by or on said patient, of said vasoactive agent, said osmolyte, and said active ingredient according to one of the methods of topical delivery described herein.

In another embodiment, a kit for topical delivery of an active ingredient to a patient includes a vasoactive agent, an osmolyte, an active ingredient, an occlusive barrier; and a set of written instructions for use, by or on the patient, of the vasoactive agent, osmolyte, and active ingredient according to one of the methods of topical delivery described herein.

In another embodiment, there is a method of manufacturing a medicament for transdermal administration. The method includes combining a vasoactive agent; an osmolyte; and an active ingredient in sufficient amounts to cause permeation of the active ingredient to at least one affected region of a patient when applied to one of the skin and other exterior region of the patient.

The following are some exemplary topical formulations, procedures for preparing the formulations, and possible uses for the formulations.

Example 1

| Component | % (w/w) |
| --- | --- |
| Thiabendazole (active ingredient) | 10 |
| Phenoxyethanol (preservative) | 0.7 |
| Menthol (penetration enhancer) | 5 |
| Eucalyptus Oil (skin conditioner) | 5 |
| Soybean Oil (penetration enhancer) | 3 |
| Cetyl Alcohol (emulsifier) | 2 |
| Glyceryl Monostearate (emulsifier) | 5 |
| Cholesterol (penetration enhancer) | 3 |
| ST Elastomer 10 (transpiration occlusive barrier) | 2 |
| Vitamin E TPGS (penetration enhancer) | 2 |
| Propylparaben (preservative) | 0.1 |
| Methyl nicotinate (vasodilator) | 0.05 |
| Lipoid. SLM 2008 (penetration enhancer) | 5 |
| $MgSO_4$ (osmolyte) | 15 |
| Methylparaben (preservative) | 0.2 |
| Allantoin (skin conditioner) | 0.2 |
| Propylene Glycol (solvent) | 2 |
| Xanthan Gum (polymer) | 1 |
| Water (solvent) | 38.75 |

Beaker 1

Weigh in Soybean Oil, Cetyl Alcohol, Glyceryl Monostearate, Cholesterol, ST Elastomer 10, Vitamin E TPGS and Propylparaben, heat to 70° C., mix until uniform.

Beaker 2

Dissolve $MgSO_4$ in one third of water, heat if necessary.

Beaker 3 (Main Beaker)

Weigh in methyl nicotinate, Lipoid SLM 2008, Methylparaben, Allantoin, and ⅔ of water, mix at high speed. Add the mixture of Propylene Glycol and Xanthan Gum into the beaker with strong mixing. Heat to 70° C. Add component in Beaker 1 into Main Beaker at 70° C. Mix for 10 minutes. Cool it down. Add Thiabendazole, Phenoxyethanol, Menthol, Eucalyptus Oil into Main Beaker at 40° C. Mix for 10 minutes. Add components in Beaker 2 into Main Beaker, mix for another 15 minutes.

Indications and Use: This formulation can be useful for the treatment of onychomycosis and other topically available fungal diseases. The user would apply approximately 2 grams of the formulation to the infected toes, rubbing the formulation until absorbed. Treatment should be done 1-2 times per day for up to 180 days.

Example 2

| Component | % (w/w) |
| --- | --- |
| Resveratrol (active ingredient) | 10 |
| Phenoxyethanol (preservative) | 0.7 |
| Menthol (penetration enhancer) | 5 |
| Eucalyptus Oil (penetration enhancer) | 5 |
| Soybean Oil (penetration enhancer) | 3 |
| Cetyl Alcohol (emulsifier) | 2 |
| Glyceryl Monostearate (emulsifier) | 5 |
| Cholesterol (penetration enhancer) | 3 |
| ST Elastomer 10 (transpiration occlusive barrier) | 2 |
| Vitamin. E TPGS (penetration enhancer) | 2 |
| Propylparaben (preservative) | 0.1 |
| Tolazine (vasodilator) | 1 |
| Lipoid SLM 2008 (emulsifier) | 5 |
| Dextrose (osmolyte) | 15 |
| Hexyl nicotinate (vasodilator) | 0.1 |
| Methylparaben (preservative) | 0.2 |
| Allantoin (skin conditioner) | 0.2 |
| Propylene Glycol (solvent) | 2 |
| Xanthan Gum (polymer) | 1 |
| Water (solvent) | 37.8 |

Beaker 1

Weigh in Soybean Oil, Cetyl Alcohol, Glyceryl Monostearate, Cholesterol, ST Elastomer 10, Vitamin E TPGS and Propylparaben, heat to 70° C., mix until uniform.

Beaker 2

Dissolve Dextrose in one third of water, heat if necessary.

Beaker 3 (Main Beaker)

Weigh in Tolazine, Lipoid SLM 2008, Methylparaben, Allantoin, Hexyl nicotinate, and ⅔ of water, mix at high speed. Add the mixture of Propylene Glycol and Xanthan Gum into the beaker with strong mixing. Heat to 70° C. Add component in Beaker 1 into Main Beaker at 70° C. Mix for 10 minutes. Cool it down. Add Resveratrol, Phenoxyethanol, Menthol, Eucalyptus Oil into Main Beaker at 40° C. Mix for 10 minutes. Add components in. Beaker 2 into Main Beaker, mix for another 15 minutes.

Indications and uses. This topical formulation can be useful for the treatment of basal cell carcinomas and other externally available cancers. The user would apply 1-3 grams of formulation to the afflicted area(s) rubbing the formulation into the skin until absorbed. Applications may be 1-2 times per day for up to 90 days.

Example 3

| Component | % (w/w) |
| --- | --- |
| Olive Oil (penetration enhancer) | 5 |
| Cetyl Alcohol (emulsifier) | 4 |
| Glyceryl Monostearate (penetration enhancer) | 5 |
| Silky Wax 10 (transpiration occlusive barrier) | 2 |
| Propylparaben (preservative) | 0.1 |
| Methyl Nicotinate (vasodilator) | 0.01 |
| $MgSO_4$ (osmolyte) | 15 |
| Ibuprofen Sodium (active ingredient) | 10 |
| Methylparaben (preservative) | 0.2 |
| Allantoin (skin conditioner) | 0.2 |
| Propylene Glycol (solvent) | 2 |
| Tetrasodium EDTA (chelator) | 5 |
| Polysorbate 80 (formulation solubilizer) | 2 |

| Component | % (w/w) |
|---|---|
| Cellosize QP 52000 H (formulation thickener) | 0.5 |
| Phenoxyethanol (preservative) | 0.7 |
| Water (solvent) | 48.29 |

Beaker 1

Weigh in Olive Oil, Cetyl Alcohol, Glyceryl Monostearate, Silky Wax 1.0, and Propylparaben, heat to 70° C., mix until it's uniform.

Beaker 2

Dissolve MgO$_4$ in one third of water, heat if necessary.

Beaker 3 (Main Beaker)

Weigh in Methyl Nicotinate, Ibuprofen Sodium, Methylparaben, Allantoin, Polysorbate 80, Tetrasodium EDTA and ⅔ of water, mix at high speed. Add the mixture of Propylene Glycol and Cellosize QP 52000H into the beaker with strong mixing, Heat to 70° C. Add component in Beaker 1 into Main Beaker at 70° C. Mix for 10 minutes. Cool it down. Add Phenoxyethanol and components in Beaker 2 into Main Beaker below 40° C., mix for another 15 minutes.

Indications and Use: This example can be useful for the topical application of ibuprofen as an anti-inflammatory agent to treat inflammatory diseases such as osteoarthritis. The user would apply approximately 2 grams of formulation to each afflicted area, massaging the formulation into the skin until absorbed. Daily use 1-3 times per day could be used as needed for relief of pain and discomfort.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A formulation for topical delivery of an active ingredient to a mammal, said mammal having a body surface and the body surface having a topical application site comprising skin, the formulation comprising:
 a vasodilator, an osmolyte, and an active ingredient, wherein:
 a) the vasodilator is selected from the group consisting of arginine, methyl nicotinate, naftidrofuryl oxalate, papaverine, tolazoline, and combinations of the foregoing,
 b) the osmolyte is a sugar;
 c) the vasodilator and the osmolyte are present in amounts effective to work together in a synergistic manner to enable penetration of the active ingredient into or through the skin;
 d) the vasodilator, the osmolyte, and the active ingredient are non-identical; and
 e) the formulation has an osmolarity that is greater than 350 milliOsmol/L.

2. The formulation of claim 1, further comprising a component selected from the group consisting of a transpiration barrier, a penetration enhancer, and a drug administration patch.

3. The formulation of claim 1, further comprising a transpiration barrier, wherein the transpiration barrier includes at least one of a chemical barrier or a physical barrier.

4. The formulation of claim 1, wherein said formulation is packaged in a water-resistant delivery system.

5. The formulation of claim 1, wherein the active ingredient is a sirtuin inhibitor.

6. The formulation of claim 1, wherein the active ingredient is a sirtuin activator.

7. The formulation of claim 1, wherein the vasodilator is methyl nicotinate.

8. A method for enhancing the penetration of an active ingredient into or through a body surface comprising skin, the method comprising administering to the skin a formulation according to claim 1.

9. The method of claim 8, wherein the active ingredient penetrates to at least one of the epidermis, a dermis, or a systemic circulatory vessel.

10. The method of claim 8, wherein the active ingredient is a sirtuin inhibitor or sirtuin activator and the region of the body surface is skin.

11. A method for topical delivery of an active ingredient to a mammal, said mammal having a body surface and said body surface comprising a dermis and a topical application site comprising skin, the method comprising:
 administering a vasodilator to the topical application site, said vasodilator being deliverable to a region of said dermis and said vasodilator being selected from the group consisting of arginine, methyl nicotinate, naftidrofuryl oxalate, papaverine, tolazoline, and combinations of the foregoing;
 administering an osmolyte to the topical application site, wherein the osmolyte is a sugar; and
 administering the active ingredient to the topical application site, wherein the vasodilator and the osmolyte are present in amounts effective to work together in a synergistic manner to enable penetration of the active ingredient into or through the skin, wherein the vasodilator, the osmolyte, and the active ingredient are non-identical and wherein the vasodilator, the osmolyte, and the active ingredient have an osmolarity that is greater than 350 milliOsmol/L.

12. The method of claim 11, wherein the vasodilator and osmolyte are applied sequentially.

13. The method of claim 11, wherein the vasodilator and osmolyte are applied together.

14. The method of claim 11, further comprising applying an occlusive barrier to the topical application site.

15. A kit for topical delivery of an active ingredient to a mammal, said kit comprising:
 i) a formulation including:
 a) a vasodilator selected from the group consisting of arginine, methyl nicotinate, naftidrofuryl oxalate, papaverine, tolazoline, and combinations of the foregoing;
 b) an osmolyte, wherein the osmolyte is a sugar;
 c) an active ingredient;
 wherein the vasodilator and the osmolyte are present in amounts effective to work together in a synergistic manner to enable penetration of the active ingredient into or through the skin,
 wherein the vasodilator, the osmolyte, and the active ingredient are non-identical and wherein the vasoactive agent, the osmolyte, and the active ingredient have an osmolarity that is greater than 350 milliOsmol/L; and
 (ii) a set of written instructions for use, by or on said mammal, of said vasodilator, said osmolyte, and said active ingredient according to the method of claim 11.

16. The formulation of claim 1, wherein the osmolarity is greater than 600 milliosmol/L.

17. The method of claim 8, wherein the osmolarity is greater than 600 milliosmol/L.

18. The method of claim 11, wherein the osmolarity is greater than 600 milliosmol/L.

19. The kit of claim 15, wherein the osmolarity is greater than 600 milliosmol/L.

20. The method of claim 11, wherein the vasodilator induces an increased blood flow in the body surface.

21. The method of claim 20, wherein the increase in blood flow is greater than 1% as measured by laser-Doppler velocimetry.

22. The method of claim 21, wherein the increase in blood flow is greater than 5%.

23. The method of claim 20, wherein the osmolyte is absorbed by the body surface and the increased blood flow works in synergy with the osmolyte to enhance penetration of the active ingredient.

24. The method of claim 11, wherein administration of the vasodilator, the osmolyte, and the active ingredient results in passage of the vasodilator through a basement membrane of the body surface.

25. The method of claim 11, wherein the administered vasodilator and the osmolyte exert a physiological change in the body surface of the mammal to thereby allow transport of the administered active agent through the body surface.

26. The method of claim 25, wherein the administered vasodilator and the osmolyte exert a physiological change in the body surface of the mammal to thereby allow transport of the administered active agent into at least one of an epidermal tissue of the body surface, a dermal tissue of the body surface, or a portion of a systemic circulatory system of the mammal.

27. The formulation of claim 1, wherein the vasodilator is tolazoline.

28. The formulation of claim 1, wherein the vasodilator is papaverine.

29. The formulation of claim 1, wherein the vasodilator is naftidrofuryl oxalate.

30. The formulation of claim 1, wherein the vasodilator is arginine.

31. The formulation of claim 8, wherein the vasodilator is methyl nicotinate.

32. The formulation of claim 8, wherein the vasodilator is tolazoline.

33. The formulation of claim 8, wherein the vasodilator is papaverine.

34. The formulation of claim 8, wherein the vasodilator is naftidrofuryl oxalate.

35. The formulation of claim 8, wherein the vasodilator is arginine.

36. The formulation of claim 11, wherein the vasodilator is methyl nicotinate.

37. The formulation of claim 11, wherein the vasodilator is tolazoline.

38. The formulation of claim 11, wherein the vasodilator is papaverine.

39. The formulation of claim 11, wherein the vasodilator is naftidrofuryl oxalate.

40. The formulation of claim 11, wherein the vasodilator is arginine.

41. The kit of claim 15, wherein the vasodilator is methyl nicotinate.

42. The kit of claim 15, wherein the vasodilator is tolazoline.

43. The kit of claim 15, wherein the vasodilator is papaverine.

44. The kit of claim 15, wherein the vasodilator is naftidrofuryl oxalate.

45. The kit of claim 15, wherein the vasodilator is arginine.

46. The formulation of claim 1, wherein the osmolyte is xylobiose.

47. The formulation of claim 1, wherein the osmolyte is galactose.

48. The formulation of claim 1, wherein the osmolyte is lactose.

49. The formulation of claim 1, wherein the osmolyte is glucose.

50. The method of claim 8, wherein the osmolyte is xylobiose.

51. The method of claim 8, wherein the osmolyte is galactose.

52. The method of claim 8, wherein the osmolyte is lactose.

53. The method of claim 8, wherein the osmolyte is glucose.

54. The method of claim 11, wherein the osmolyte is xylobiose.

55. The method of claim 11, wherein the osmolyte is galactose.

56. The method of claim 11, wherein the osmolyte is lactose.

57. The method of claim 11, wherein the osmolyte is glucose.

58. The kit of claim 15, wherein the osmolyte is xylobiose.

59. The kit of claim 15, wherein the osmolyte is galactose.

60. The kit of claim 15, wherein the osmolyte is lactose.

61. The kit of claim 15, wherein the osmolyte is glucose.

62. The formulation of claim 1, wherein the active ingredient is ibuprofen.

63. The formulation of claim 1, wherein the active ingredient is acetaminophen.

64. The formulation of claim 1, wherein the active ingredient is benfotiamine.

65. The method of claim 8, wherein the active ingredient is ibuprofen.

66. The method of claim 8, wherein the active ingredient is acetaminophen.

67. The method of claim 8, wherein the active ingredient is benfotiamine.

68. The method of claim 11, wherein the active ingredient is ibuprofen.

69. The method of claim 11, wherein the active ingredient is acetaminophen.

70. The method of claim 11, wherein the active ingredient is benfotiamine.

71. The kit of claim 15, wherein the active ingredient is ibuprofen.

72. The kit of claim 15, wherein the active ingredient is acetaminophen.

73. The kit of claim 15, wherein the active ingredient is benfotiamine.

* * * * *